United States Patent [19]

Cohen

[11] 4,293,652

[45] Oct. 6, 1981

[54] METHOD FOR SYNTHESIZING DNA SEQUENTIALLY

[75] Inventor: Stanley N. Cohen, Portola Valley, Calif.

[73] Assignee: Cetus Corporation, Berkeley, Calif.

[21] Appl. No.: 42,403

[22] Filed: May 25, 1979

[51] Int. Cl.³ .............................................. C12N 15/00
[52] U.S. Cl. ..................................... 435/172; 435/91; 435/68; 435/820; 536/27
[58] Field of Search ............................ 435/172, 91, 92

[56] References Cited

PUBLICATIONS

Itakura et al., Science, vol. 198, pp. 1056-1063 (1977).
Goebel et al., Genetic Engineering edited by Boyer et al., Elsevier/North-Holland Biomedical Press, pp. 47-58 (1978).
Greene et al., Methods in Molecular Biology, Chapter 4, pp. 87-111.
Hershfield et al., Proc. Natl. Acad. Sci., vol. 71, pp. 3455-3459 (1974).
Kleid et al., Proc. Natl. Acad. Sci., vol. 73, pp. 293-297 (1975).
Cohen et al., Proc. Natl. Acad. Sci., vol. 70, pp. 3240-3244 (1973).
Khorana et al., J. Mol. Biol., vol. 72, pp. 209-217 (1972).
Agarwal et al., Nature, vol. 227, pp. 27-34 (1970).
Khorana et al., J. Biol. Chem., vol. 251, pp. 565-570 (1976).
Carbon et al., Proc. Natl. Acad. Sci., vol. 72, pp. 1392-1396 (1975).
Polisky et al., Proc. Natl. Acad. Sci., vol. 73, pp. 3900-3902 (1976).
Maxam et al., Proc. Natl. Acad. Sci., vol. 74, pp. 560-564 (1977).
Sgaramella et al., J. Mol. Biol., vol. 72, pp. 427-444 (1972).
Itakura et al., J. Biol. Chem., vol. 250, pp. 4592-4597 (1975).

*Primary Examiner*—Alvin E. Tanenholtz
*Attorney, Agent, or Firm*—Fitch, Even, Tabin, Flannery & Welsh

[57] ABSTRACT

A method and a DNA linker are described for synthesizing relatively long double-stranded deoxyribonucleic acid sequences of defined composition. Short complementary single strand segments of oligonucleotides comprising part of the full sequence desired are synthesized using known procedures. Overlapping single strand segments are annealed forming double-stranded fragments which are inserted in cloning vectors and cloned in an appropriate host, both purifying the DNA fragments and amplifying the amount thereof. An adjacent fragment is then similarly synthesized in quantity and such fragments are inserted adjacent to the first synthetic introduced fragments in the cloning vectors, followed by cloning in an appropriate host. The procedure continues until the entire desired sequence has been formed, at which time it may be excised or cloned directly in the vectors upon which it was made. The described DNA linker contains a restriction enzyme recognition sequence for a restriction enzyme which cuts offset from the recognition sequence and exactly at the end of the linker, enabling synthesized DNA to be inserted at the end of the linker without disturbing the recognition sequence.

4 Claims, 5 Drawing Figures

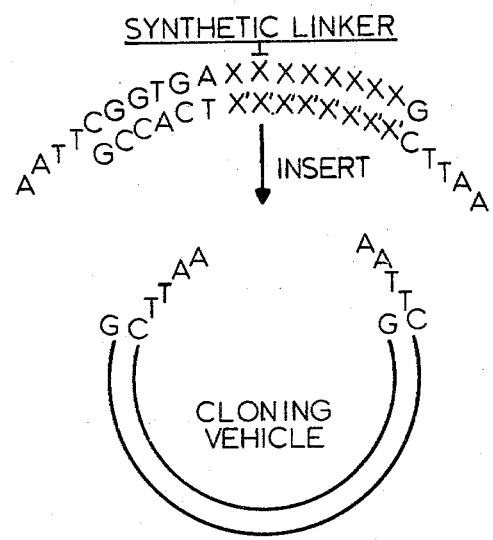
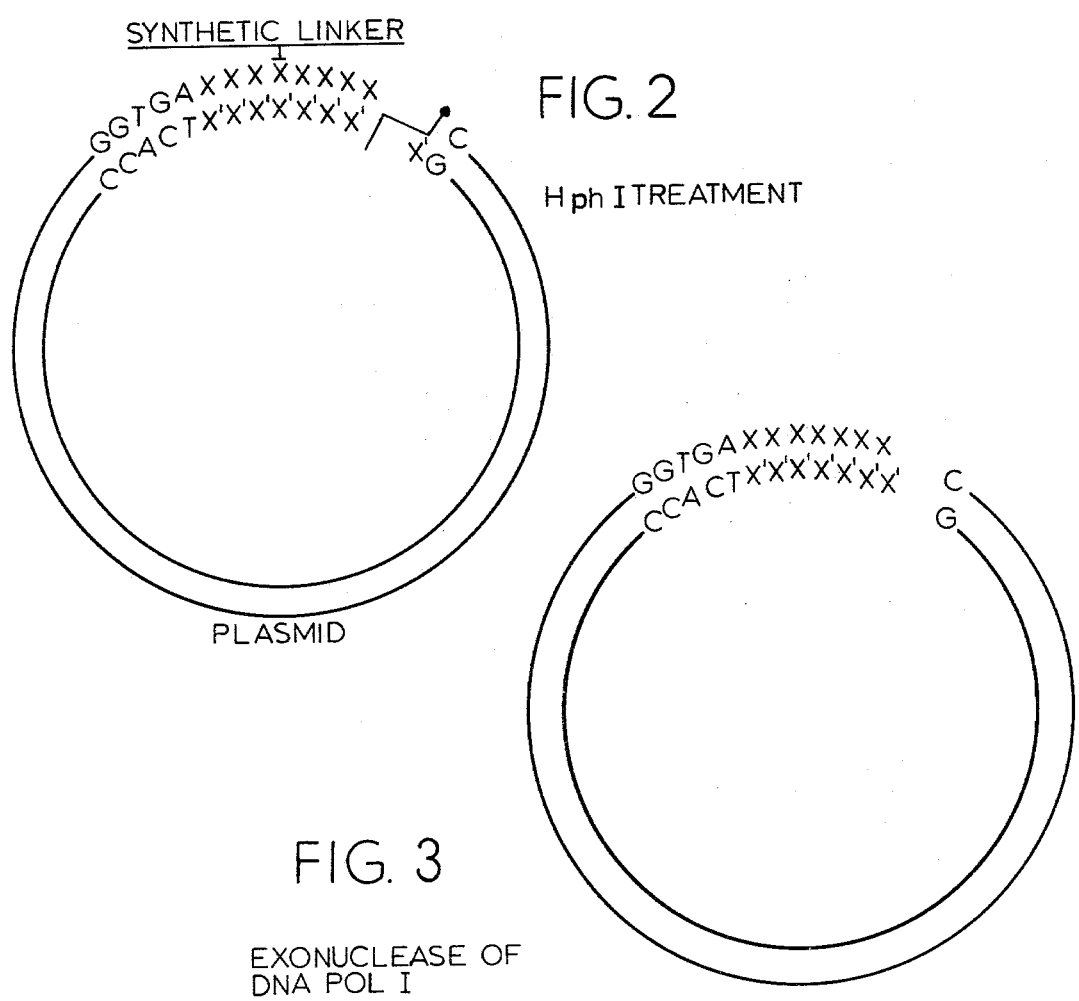

FIG. 4-A
NEW SYNTHETIC FRAGMENT
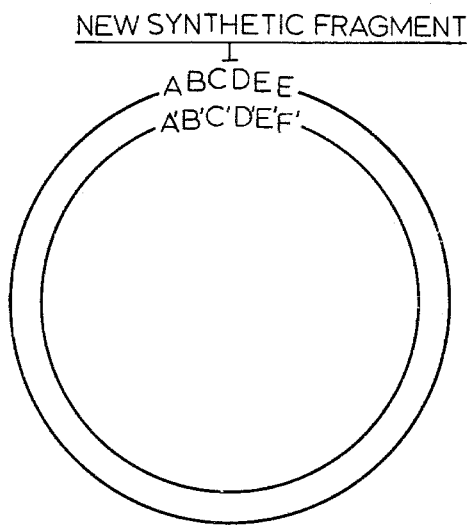
FIG. 4-B
NEW SYNTHETIC FRAGMENT
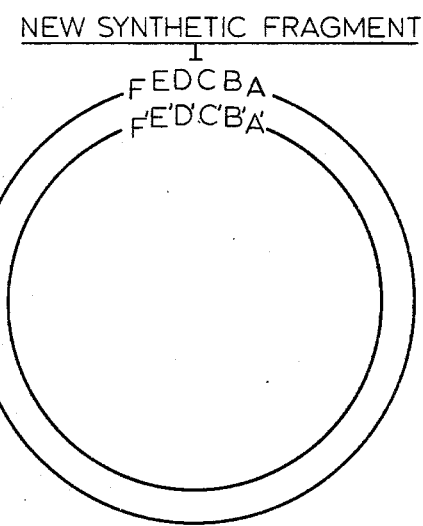
OR
LIGATION OF 1st FRAGMENT
FIG. 4
FIG. 5
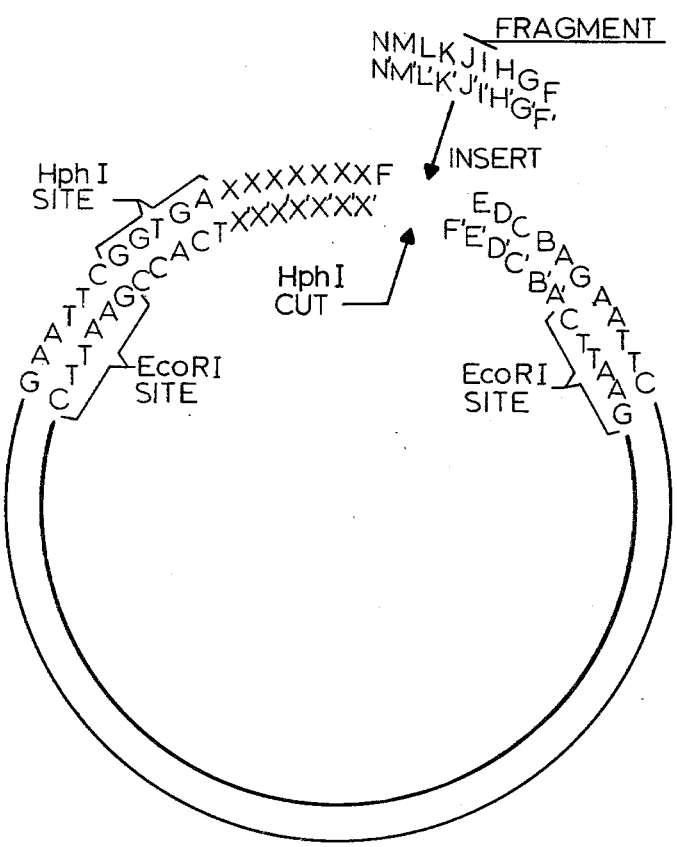

METHOD FOR SYNTHESIZING DNA SEQUENTIALLY

This invention relates to recombinant DNA technology and, more particularly, to an improved technique for synthesizing long double-stranded DNA molecules.

The rapidly developing art of recombinant DNA technology enables the introduction of genetic information into a foreign host and expression of this formation in the new host. The genetic information may be DNA selected from or isolated from another organism or it may be DNA which is synthesized chemically by any of a variety of known methods. The chemical synthesis of DNA permits the production of genes which otherwise might be very difficult to retrieve from the cell in which they naturally originate.

Chemical synthesis of DNA molecules typically involves the synthesis of two different single strands of nucleotides which are complementary to each other. These are then joined together at the complementary base pairs to form the double-stranded DNA molecule. The single strand fragments may be formed by a number of known chemical schemes, for example, the phosphodiester procedure of Khorana et al (*J. Mol. Biol.*, 72:209) and phosphotriester method of Narang et al (*J. Biol. Chem.*, 250:4592).

Although known chemical synthesis techniques for DNA have been successful, some difficulties arise in making individual DNA chains longer than about 10-15 nucleotide bases. This is because the yield from known chemical synthesizing techniques typically declines as the length of the synthesized nucleotide chain increases. The solution to this problem has been to synthesize fragments which are less than the full length of DNA desired to be synthesized, and to subsequently join the fragments together to form the desired relatively long DNA molecule. Two basic schemes for accomplishing this have been employed.

A scheme for building long double-stranded molecules from short single-stranded fragments was described by Khorana's group in connection with transfer RNA genes for alanine (*Nature*, 227:27) and tyrosine (*J. of Bio. Chem.*, 251:565). Khorana's group took advantage of the property of base complementarity while doing the construction in stages. A short double-stranded polymer corresponding to part of the desired gene was formed by chemical synthesis. Once such short gene segments were made in sufficient quantity and their proper sequence verified, they were set aside and another segment of the desired gene was synthesized, verified, and made in quantity. Once all of the parts were available, they were ligated together to form the complete molecule.

Although the Khorana et al technique can be adapted for the synthesis of any gene, regardless of length, it is a laborious and time consuming process. Conditions for each reaction mixture must be optimized to provide sufficient yields. A large amount of material must be used in the first stage reactions to assure sufficient reactants of the correct composition for subsequent steps. The results of the technique are frequently unpredictable and yields may vary widely. Finally, the reactions typically do not ever go to completion, that is, all fragments capable of forming the complete molecules are usually not used up.

In *Science*, 198:1056, Itakura et al describe a scheme for building long double-stranded DNA molecules from shorter single-stranded chemically synthesized fragments. In chemically synthesizing the gene for the hormone somatostatin, single strand oligonucleotides 11–16 bases long were synthesized, each corresponding to a portion of a single strand of the complete somatostatin molecule. The various fragments synthesized were selected so that the fragments from one strand overlapped fragments from the opposite strand, that is, that each fragment from the Watson strand contained bases complementary to the base on at least two of the fragments from the Cricks strand. These fragments were all put in a reaction mixture with the expectation that base pairing between complementary bases on separate fragments would cause the fragments to line up in correct order and form a complete sequence held together by hydrogen bonds. These bonds were then covalently linked, using ligase, to complete the somatostatin gene.

The foregoing described technique works effectively for relatively small genes, such as somatostatin. However, adapting the foregoing described methology to the synthesis of relatively longer DNA molecules is difficult. The T4 ligase, the enzyme used to seal the molecules into one piece, is known to make mistakes at a significant frequency in that it does not demand exact base pairing to seal pieces together. Thus, two fragments which have just partial homology may align briefly and be ligated. With a few fragments such as required with relatively short genes, this problem is not particularly significant, as most of the ligated molecules will be in the proper and complete homology. As the length of the DNA being synthesized increases, however, so does the probability of error. Khorana et al (*J. Bio. Chem.*, 251:565) report that no more than eight segments or fragments (the number used in Itakura's somatostatin synthesis) could be used in a one step joining reaction without ambiguity.

Another problem exists in connection with the foregoing described procedure because of the high probability of error in homology of the ligated fragments. Strong selection procedures or sophisticated methods of detection must be employed on the cloned product in order to find those cells that are accurate copies of the synthesized gene. However, this is not always feasible. Known selection procedures often recognize the products of only a small part of a molecule. For example immunological techniques identify polypeptides on the basis of small sections which act as immunological determinants. Substantial numbers of peptides could be in error elsewhere, and would therefore not be noticed and would be selected anyway.

It is possible to determine which clones contain DNA molecules having the correctly aligned fragments by sequencing the bases. Indeed DNA sequencing is typically used for verification of the polynucleotide (DNA) product. To use sequencing, however, for the purpose of screening involves an impractical amount of work and time since hundreds of thousands of samples might have to be tested to find a correct one.

It is an object of the present invention to provide an improved method for synthesizing gene-length segments of double-stranded DNA.

Another object of the invention is to provide an improved method for producing cloning vectors containing sections of synthesized DNA.

A further object of the invention is to provide an improved DNA linker which facilitates the synthesis of double-stranded DNA segments.

A further object of the invention is to provide a method for synthesizing double-stranded DNA which is highly efficient, provides for convenient purification as the synthesis proceeds, and provides amplification of the amount of new material for synthesis at each step.

Various other objects of the invention will become apparent to those skilled in the art from the following description, taken in connection with the accompanying drawings wherein:

FIG. 1 is a schematic view of a plasmid and a DNA linker as used in one form of practicing the method of the invention;

FIG. 2 illustrates the plasmid cloning vehicle of FIG. 1 with the DNA linker inserted therein and broken by treatment with a particular type of restriction enzyme;

FIG. 3 illustrates the plasmid configuration of FIG. 2 after treatment to provide blunt ends;

FIG. 4 illustrates the plasmid of FIG. 3 in which a synthetic fragment is incorporated, showing both orientations of incorporation by blunt end ligation; and FIG. 5 illustrates further opening of the plasmid of FIG. 4 for insertion of a further fragment and with the further fragment shown in exploded position.

Very generally, the method of the invention comprises synthesizing a fragment of double-stranded DNA corresponding to a preselected portion of the full length of DNA desired. This fragment is inserted into a cloning vector and is amplified and purified by cloning. The procedure is then repeated for another fragment corresponding to a further preselected portion of the desired DNA until all portions have been inserted in the cloning vector to complete the desired DNA sequence.

More particularly, the method of the invention builds the DNA molecules directly within the cloning vector. In a preferred form of the method, complementary oligonucleotides are synthesized using a known procedure. These are annealed forming a double-stranded fragment. The vector is opened and the fragment of synthesized double-stranded DNA is inserted. After closing, the vector is cloned in an appropriate host, both purifying the synthetic DNA, by forming colonies derived from single instances of insertions; and amplifying the amount of the synthesized DNA by the replication process. The vector is then opened again, in one approach utilizing a unique class of restriction enzyme to cut exactly at the end of the first synthetic piece. Another synthesized double-stranded fragment of DNA can then be inserted. The vector is closed again and cloned. The process is repeated until the entire desired DNA molecule has been constructed, at which time it may be excised or cloned directly upon the vector with which it was made.

The cloning vehicles used in the method of the invention may be of any appropriate type. The plasmid or virus cloning vehicle selected should be stable in a suitable host, should have incorporated in it a replicator locus and genes capable of allowing replication of the vector, and should carry a phenotypic property allowing selection of transformed host. In addition, the cloning vehicle should have a single recognition sequence for a preselected restriction enzyme, and it should be absent any recognition sequence at all for one of the particular restriction enzymes of the type that cut at a site downstream or offset from the recognition sequence. The single recognition sequence for the preselected restriction enzyme should not be such that the cut occurs in a needed informational region of the vector, as the exogenous or synthetic DNA will be inserted at that point. One vector satisfying the above requirments is the plasmid pBGP-120 modified so as not to be cut by the enzyme HphI. This plasmid contains a single restriction site for the enzyme EcoRI.

The plasmid cloning vector which is selected is modified by inserting therein a DNA linker, that is, a DNA segment having a particular nucleotide sequence. The DNA linker or insertion bridge, which may be synthesized by known techniques, is characterized by having a respective portion of a restriction enzyme recognition sequence at each of its ends corresponding to the separable portions of the single standard restriction enzyme recognition sequence in the cloning vehicle. Alternatively, the ends may be blunt with nucleotides suitable for blunt end ligation. In the foregoing example, pBGP120, the synthetic DNA linker would thus have a portion of an EcoRI enzyme recognition sequence at each end capable of linking with the open sticky ends of the severed EcoRI recognition sequence in the plasmid pBGP120. Alternatively, insertion of the linker in the vector can be accomplished by adding dAT or dGC tails. Between the two ends of the linker is built the recognition sequence for the restriction enzyme that cuts offset or downstream from the recognition sequence—in the example HphI. The enzyme HphI has the recognition sequence GGTGA. It cuts asymmetrically eight base later on the plus strand and seven bases later on the minus strand. In addition to the recognition sequence in the linker between the ends, a spacer is included in the synthetic DNA linker which is at least the same number of nucleotides long as the cutting site of the offset cutting restriction enzyme. Thus, in the case of the enzyme HphI, the linker includes eight bases X on the plus strand and eight bases X' on the minus strand following the HphI recognition sequence. This example is illustrated in FIG. 1.

It may also be preferred to incorporate, in the DNA linker, appropriate nucleotides for initiating transcription and translation of the synthesized DNA segments which are later appended to it, as described below. This is, in fact, necessary if the cloning vector itself does not have such nucleotides conveniently located for the correct reading frame. Thus the DNA linker would be synthesized to include a promotor for transcription, a ribosome binding site, and translational start codon. Extra codons may also be employed in the linker to shift the reading frame as desired.

In some cases, the method of the invention may be practiced without the need for a DNA linker as described. If the cloning vector has an existing recognition site for an offset cutting enzyme, it may be possible to use such a vector directly, without the need to construct a linker.

Once the cloning vector is selected and appropriately modified, if necessary, as described above, the method of the invention proceeds by preselecting a portion of the required or desired DNA strand and synthesizing it. The selected portion is the first block of nucleotides of the desired DNA molecule and is less than sixteen bases long for convenience in synthesizing by presently known techniques. This preselected DNA fragment is synthesized in any suitable manner, such as by synthesizing the individual complementary single strands and annealing them to form the desired double-stranded DNA fragment. The plasmid cloning vehicle is cut by the offset cutting restriction enzyme (HphI in the example) as shown in FIG. 2. The cut cloning vehicle is then treated with a single strand specific exonuclease to remove the single-stranded tails, or is treated with DNA polymerase to fill in the missing nucleotides. In the illustrated case, one base is removed on each end of the cut cloning vehicle. In the illustrated embodiment, since the single-stranded portions are on 3' ends, the exonuclease of DNApolI can be used. The result is shown in FIG. 3.

The open cloning vehicle, now with blunt ends, then has the first synthesized gene fragment inserted therein by blunt end ligation. Two possible results are illustrated in FIG. 4 (A and B), depending upon the orientation of the inserted fragment. Only one of the possibilities, the one in FIG. 4B is useful. The plasmid or cloning vehicle, including the inserted DNA fragments, are then placed in appropriate hosts and growth conditions are provided for the hosts to amplify and purify the inserted fragments. The cloning vehicles are then harvested from the colonies and are cut with the offset cutting restriction enzyme. The particular desired orientation (the configuration in FIG. 4B) is then verified by partial sequencing.

The foregoing procedure is then repeated by synthesizing the next fragment of the desired DNA sequence, and blunt end ligating it into the cloning vehicle. The two fragment portions of the desired DNA are then amplified and purified by growing colonies. In the particular example it should be noted that the last nucleotide (F-F' in FIG. 5) is lost by the removal of the single-stranded portions and is therefore included in the second synthesized fragment.

After the second fragment is inserted, once again two different orientations are possible. The correctly placed or oriented pieces may be found after sequencing and cloning as before. Note that once a fragment has been placed accurately, it need not be sequenced again as it is carried on in the same orientation in future steps. The foregoing described procedure continues with cloning, cutting and blunt end ligation of new synthetic pieces or fragments until the desired whole gene has been produced.

EXAMPLE 1

Human insulin B chain may be synthesized as follows:

(a) The plasmid pBGP120 is modified so as not to be cut by the enzyme HphI by a procedure analogous to the procedure used to remove unwanted EcoRI sites described by Carbon et al (*PNAS*, 72:1392). A DNA linker as described above is inserted at the single EcoRI site. EcoRI restriction enzyme digestion is accomplished as described by Greene et al (*Methods Mol. Bio.*, 7:78).

(b) Single-stranded DNA oligonucleotides TTTGTC and AAACAG are synthesized by the triester method of Narang et al (*JBC* 250:4592). These single strands are annealed complementary to each other to form a double-stranded DNA fragment. DNA ligation is accomplished with DNA ligase using the conditions of Herschfeld et al (*PNAS* 71:3455).

(c) Removal of the single-stranded DNA tails may be accomplished by utilizing any number of exonucleases such as ExoVII, SI, and DNA PolI 3' exoactivity, to name a few. For 5' tails the SI procedure is appropriate. One µl containing 0.1 µg of DNA is mixed with 2.3 units SI in a total reaction volume of 25 µl containing 0.3 M sodium chloride, 4.5 mM zinc chloride, and 0.03 M sodium acetate at pH 4.0. After 30 minutes at 26° C. the reaction is stopped with 10 µl of 0.25 M Tris hydrogen chloride at pH 8.1. For 3' tails, as in the example with HphI, the preferable enzyme is the DNA PolI 3' exonuclease activity. Here, two µl containing one µg of DNA is mixed with 0.5 µl of Boehringer Mannheim DNA polymerase (900 units/ml) and with 5.25 µl of buffer 19 mM potassium chloride, 95 mM Tris Hcl at pH 7.8, 13 mM magnesium chloride, and 19 mM of ammonium chloride. The mixture is incubated at 26° C. for one hour. Then there is added 0.5 mM each of dATP, dTTP, dCTP, and dGTP to repair excessive digestion. The mix is incubated further two hours.

(d) The double-stranded DNA fragments are inserted as illustrated by bases A-F in FIG. 3. HphI restriction enzyme digestion is done as described by Kleid et al (*PNAS* 73:293). Blunt end DNA ligation follows the procedures of Sgamarella and Khorana (*JMB* 72:427).

(e) Transformations of the host are accomplished as described by Cohen et al (*PNAS* 70:3240) and the hosts are incubated and grown as appropriate.

(f) Identification of the orientation of the cloned fragments may be accomplished as described by Polisky et al (*PNAS* 73:3900) and the DNA sequencing may be done by the method of Maxam and Gilbert (*PNAS* 74:560).

(g) Following successful insertion of the first DNA fragment as described above, insertion of further fragments may follow the identical procedure using the following "coding" strands (the non-coding strand is made up of the similar sequence of complementary bases); TTTGTC, CAATCAGCA, ACCTTTGTG, GGTCCTCAC, CCTGGTGGA, AGGCTC, CTGTACCTG, GGTGTGTGG, GGGAACGTG, GGTTTCTTC, TCTACACCC.

EXAMPLE II

The synthesis of a gene for insulin A chain can be accomplished with the identical procedure using the following fragments: GGCATTGTG, GGATCAGTG, GCTGCACCA, AGCATCTGC, CTCCCTCTA, ACCAACTGG, GAGAACTAC, CTGCAAC.

EXAMPLE III

The synthesis of a gene for the human hormone ACTH can be accomplished similarly using the following fragments: TCTTACTCC, CATGGAACA, ACTTCCGCT, TGGGGCAAG, GCCGGTGGG, GCAAGAAGC, CGGCGCCCG, GGTGAAGGT, TGTACCCCA, AACGGCGCC, CGAGGACGA, AGTCGGCCC, CAGGCCTTT, TCCCTCGA, AATC.

It may be seen, therefore, that the invention provides an improved technique for synthesizing long DNA chains that is far more efficient and reliable than those methods previously known. The invention accomplishes the sequential building of large polymeric DNA directly on a cloning vector, allowing for the purification of the DNA and the amplification of the amount of DNA for use in building the large molecules.

Various modifications of the invention in addition to those shown and described herein will become apparent to those skilled in the art from the foregoing description and accompanying drawings. Such modifications are intended to fall within the scope of the appended claims.

What is claimed is:

1. A method for producing a cloning vector containing a synthesized gene of a predetermined composition and length, comprising, preparing or selecting a cloning vector having a single restriction enzyme recognition sequence for a restriction enzyme of the type which cuts at a site outside said recognition sequence, chemically synthesizing a fragment of double-stranded DNA corresponding to a preselected portion of said gene, inserting said fragment in said cloning vector, respectively, at the site cut by the restriction enzyme recognized by said restriction enzyme recognition sequence, placing said cloning vector in an appropriate host and providing growth conditions for said host to amplify and purify said inserted fragment, and repeating the foregoing said synthesis, insertion, and amplification steps for preselected portions of said gene immediately adjacent the previously cloned fragment until a gene is complete.

2. A method according to claim 1 wherein said cloning vector is prepared by inserting therein DNA linkers each having a full restriction enzyme recognition site for a restriction enzyme which cuts offset from the site, and each having a spacer section corresponding in length to the cutting location of said restriction enzyme.

3. A method according to claim 1 wherein said chemically synthesized fragments are less than 16 nucleotides long.

4. A method according to claim 1 wherein said restriction enzyme recognition sequence is for a restriction enzyme selected from the group consisting of HphI, MboII, HgaI, and MnlI.